United States Patent [19]
Yeager et al.

[11] Patent Number: 5,939,438
[45] Date of Patent: Aug. 17, 1999

[54] INSECTICIDAL OXIMINO AND HYDRAZONO DERIVATIVES OF N-BENZYL-4-BENZHYDRYL-AND N-BENZYL-4-BENZHYDROL-PIPERIDINES

[75] Inventors: Walter H. Yeager, Yardley, Pa.; Ian R. Silverman, Moorestown, N.J.; Robert N. Henrie, II, East Windsor, N.J.; Thomas G. Cullen, Milltown, N.J.; Clinton J. Peake, Trenton, N.J.

[73] Assignee: FMC Corporation

[21] Appl. No.: 09/150,424

[22] Filed: Sep. 9, 1998

Related U.S. Application Data

[60] Provisional application No. 60/059,150, Sep. 17, 1997.
[51] Int. Cl.⁶ .......................... A01N 43/40; C07D 211/26; C07D 211/28; C07D 211/18
[52] U.S. Cl. .......................... 514/331; 546/229; 546/231; 546/232; 546/235
[58] Field of Search ..................................... 546/229, 231, 546/232, 235; 514/331

[56] References Cited

U.S. PATENT DOCUMENTS 5,569,664  10/1996  Silverman et al. ...................... 514/317
5,639,763   6/1997  Silverman et al. ...................... 514/321

*Primary Examiner*—Mukund J. Shah
*Assistant Examiner*—Bruck Kifle
*Attorney, Agent, or Firm*—Ian R. Silverman; FMC Corporation

[57] ABSTRACT

It has now been found that certain novel oximino and hydrazono derivatives of N-benzyl-4-benzhydryl- and 4-benhydrolpiperidines, and their corresponding N-oxides and agriculturally acceptable salts are useful as insecticides. These compounds are represented by Formula I:

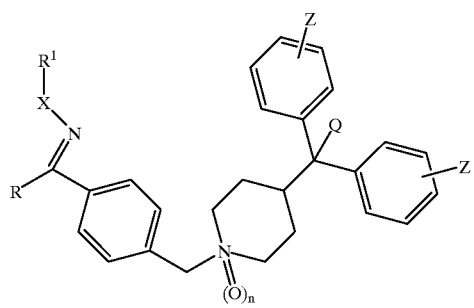

where R is hydrogen, halogen, alkyl, alkoxy, dialkylamino; $R^1$ is hydrogen, alkyl, haloalkyl, alkoxyalkyl, alkylcarbonyl and alkylaminocarbonyl; X is oxygen, or $NR^2$, Q is fluoro and hydroxy; Z is halogen, haloalkyl, haloalkoxy, pentahalothio, haloalkylthio, haloalkylsulfinyl, haloalkylsulfonyl, and —$OCF_2O$— attached to two adjacent carbon atoms of the phenyl ring; n is 0 or 1; and, when X is $NR^2$, $R^2$ is hydrogen, alkyl, alkylcarbonyl, alkoxycarbonyl, or $R^1$ and $R^2$ taken together may be —$C_mH_{2m}$, or —$C_2H_4OC_2H_4$—, where m is 3–9. Preferred compounds include those where R is hydrogen; $R^1$ is alkyl; Q is hydroxy; X is oxygen; and Z is trifluoromethyl or trifluoromethoxy.

20 Claims, No Drawings

INSECTICIDAL OXIMINO AND HYDRAZONO DERIVATIVES OF N-BENZYL-4-BENZHYDRYL-AND N-BENZYL-4-BENZHYDROL-PIPERIDINES

This application claims the benefit of U.S. Provisional Application No. 60/059,150, filed Sep. 17, 1997.

BACKGROUND OF THE INVENTION

This invention relates generally to insecticidal compounds and methods for their use in controlling insects. In particular, it pertains to insecticidal oximino and hydrazono derivatives of N-benzyl-4-benzhydryl- and N-benzyl-4-benzhydrolpiperidines where the oximino and hydrazono groups are substituted at the 4-position of the benzyl ring, and the corresponding N-oxides of the piperidines. This invention also pertains to the agriculturally acceptable salts of these compounds and their compositions that are useful in controlling insects in agricultural crops.

There is a continuing demand for new insecticides that are safer, more effective, and less costly. Insecticides are useful for controlling insects which may otherwise cause significant damage to crops such as wheat, corn, soybeans, potatoes, and cotton, to name a few. For crop protection, insecticides are desired that can control the insects without damaging the crops, and that have no deleterious effects to other living organisms, such as mammals.

U.S. Pat. Nos. 5,569,664 and 5,639,763 disclose a class of piperidine derivatives for use as insecticides:

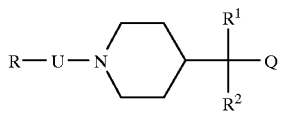

in which, among others,

U is —$(CH_2)_n$— where n is 1, 2, or 3;

Q is fluoro or hydroxy;

R is selected from a heterocycle having 5 or 6 ring atoms, optionally fused to a benzene ring, and

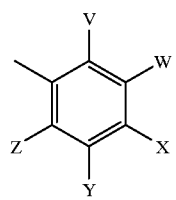

where

V, W, Y, and Z are hydrogen; and,

X is hydrogen, hydroxy, halogen, alkyl, alkoxyalkyl, alkoxy, cycloalkylalkoxy, haloalkoxy, alkenyloxy, haloalkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkylcarbonyl, alkoxycarbonylamino, alkoxycarbonyl, alkylaminocarbonyl, aminocarbonyloxy, phenyl, phenylalkoxy, phenoxy, phenoxyalkyl, or a five- or six-membered heterocycle; each cycloalkyl moiety, heterocycle, or phenyl ring is optionally substituted with halogen, alkoxy, or haloalkoxy;

W and X taken together may be —$OCH_2CH_2O$—, —$CH_2C(CH_3)_2O$—, —$OC(CH_3)_2O$—, —$N=C(C_2H_5)O$—, or —$CH=CHCH=C$—;

$R^1$ and $R^2$ are independently selected from phenyl substituted with one or more haloalkyl or haloalkoxy.

The '664 and '763 patents do not disclose insecticidal oximino or hydrazono derivatives.

SUMMARY OF THE INVENTION

It has now been found that certain novel oximino and hydrazono derivatives of N-benzyl-4-benzhydryl- and 4-benzhydrolpiperidines, and their corresponding N-oxides and agriculturally acceptable salts are useful as insecticides. These compounds are represented by Formula I:

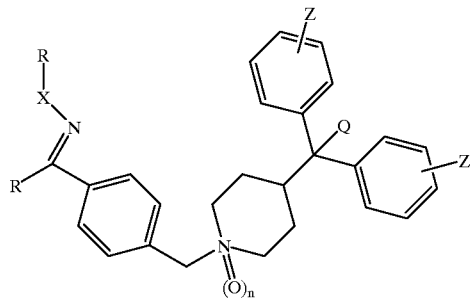

where R, $R^1$, X, and Z are substituents described below. Preferred compounds include those where R is hydrogen; $R^1$ is alkyl; Q is hydroxy; X is oxygen; and Z is trifluoromethyl or trifluoromethoxy.

DETAILED DESCRIPTION OF THE INVENTION

Certain novel oximino and hydrazono derivatives of N-benzyl-4-benzhydryl- and 4-benzhydrolpiperidines, their corresponding N-oxides and their agriculturally acceptable salts are useful in controlling insects. These compounds are represented by formula I:

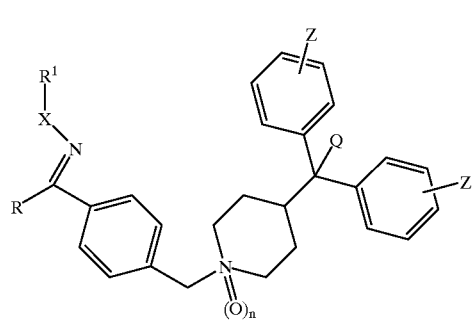

where

R is hydrogen, halogen, alkyl, alkoxy, dialkylamino;

$R^1$ is hydrogen, alkyl, haloalkyl, alkoxyalkyl, alkylcarbonyl and alkylaminocarbonyl;

Q is fluoro or hydroxy;

X is oxygen or $NR^2$;

Z is halogen, haloalkyl, haloalkoxy, pentahalothio, haloalkylthio, haloalkylsulfinyl, haloalkylsulfonyl, and —$OCF_2O$— attached to two adjacent carbon atoms of the phenyl ring;

n is 0 or 1; and, when X is $NR^2$, $R^2$ is hydrogen, alkyl, alkylcarbonyl, alkoxycarbonyl, or $R^1$ and $R^2$ taken together is —$C_mH_{2m}$, or —$C_2H_4OC_2H_4$—, where m is 3–9.

Preferred compounds are those where R is hydrogen; $R^1$ is alkyl; Q is hydroxy; X is oxygen; Z is trifluoromethyl or trifluoromethoxy; and n is 0 or 1.

A particularly preferred compound is N-[4-(ethoxyiminomethyl)phenylmethyl]-4-[bis(4-trifluoromethoxyphenyl)hydroxymethyl]piperidine N-oxide.

As used in this specification and, unless otherwise indicated, the term "alkyl" and "alkoxy" used alone or as part of a larger moiety includes 1 to 6 carbon atoms either straight or branched chain. "Halogen" refers to chlorine, bromine, and fluorine. The term "TEA" refers to triethylamine, "DMSO" refers to dimethyl sulfoxide, "DMF" refers to N,N-dimethylformamide, "DAST" refers to diethylaminosulfur trifluoride, and "NCS" refers to N-chlorosuccinimide.

The oximino and hydrazono derivatives of Formula I may be prepared by methods described below or by methods known in the art for similar compounds.

Scheme 1

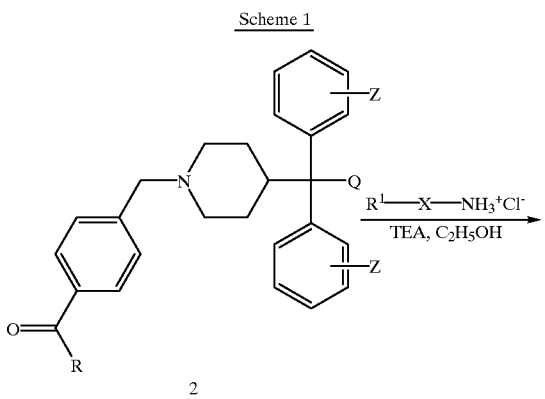

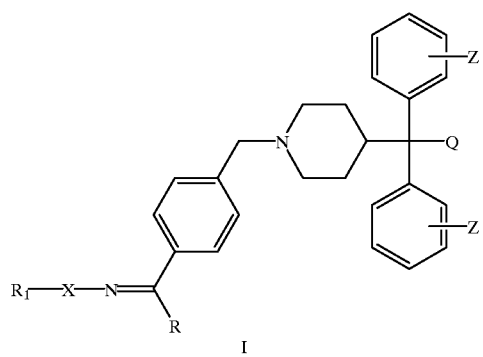

Scheme 1 shows one approach to preparing compounds of the present invention where R is hydrogen or alkyl. In general, N-benzyl-4-benzhydryl- or N-benzyl-4-benzhydrolpiperidines may be prepared as described in U.S. Pat. No. 5,569,664 by reacting a 4-benzhydryl- or a 4-benzhydrolpiperidine with a benzyl halide. In an analogous manner, a benzyl halide having in the para position a carboxaldehyde or keto group may be treated with a 4-benzhydryl- or a 4-benzhydrolpiperidine to provide intermediate 2. For example, 4-bromomethylbenzaldehyde or 4'-(bromomethyl)acetophenone may be treated with 4-[bis(4-trifluoromethoxyphenyl)hydroxymethyl]piperidine under basic conditions in a suitable solvent such as DMSO, affording 2 where Z is trifluoromethoxy and R is formyl or acetyl. Intermediate 2 may then be condensed with a hydrazine or alkoxyamine, such as methoxylamine hydrochloride or 1,1-dimethylhydrazine, to provide I.

Scheme 2

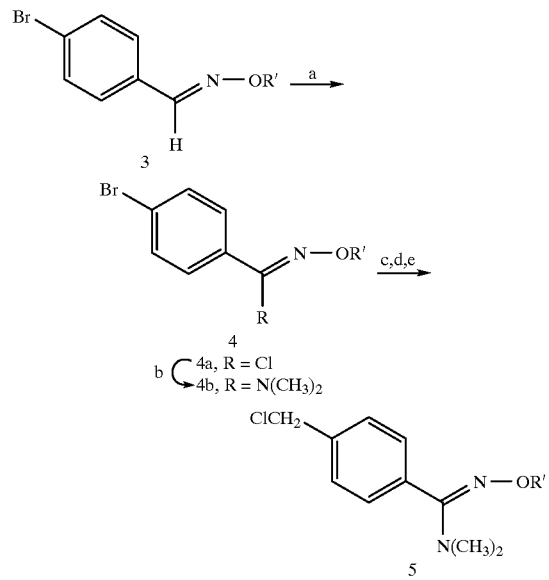

(a) NCS, HCl (gas), DMF (b) HN(CH$_3$)$_2$, THF (c) n-BuLi, DMF, THF (d) NaBH$_4$, C$_2$H$_5$OH (e) SOCl$_2$, Pyridine Scheme 2 shows another approach to compounds of the present invention where the oximino or hydrazono groups are introduced earlier in the synthesis. As an example, an oxime ether of 4-bromobenzaldehyde 3 may be chlorinated as shown in step (a) and then treated with a dialkylamine according to step (b) to provide an amidine ether intermediate 4. The bromine of 4 may be replaced by a chloromethyl group in three steps: (c) adding DMF to a lithiated species to provide the corresponding benzaldehyde, (d) reduction to the benzyl alcohol, and (e) chlorination to the benzyl chloride 5. Benzylation of a 4-benzhydrolpiperidine with benzyl chlorides 5 as described above provide further compounds of the present invention.

The N-benzyl-4-benzhydrolpiperidines I or 2 (Q is hydroxy) may be further transformed into the benzhydryl fluorides I (Q is fluoro) using either DAST or HF-pyridine.

The n-oxides I (n=1) are prepared by the treatment of the parent piperidine compound I (n=0) with 30% hydrogen peroxide in a suitable solvent. In addition the agriculturally acceptable salts are also prepared by methods similar to those known in the art for similar compounds.

A procedure for a method useful to prepare compounds of this invention is given in the example below.

EXAMPLE 1

Synthesis of N-[4-(ethoxyiminomethyl) phenylmethyl]4-[bis(4-trifluoromethoxyphenyl) hydroxymethyl]piperidine (Compound 15)

A solution of 1.0 gram (0.0018 mole) of N-[4-formylphenylmethyl]4-[bis(4-trifluoromethoxyphenyl) hydroxymethyl]piperidine, 1.8 grams (0.018 mole) of O-ethylhydroxylamine hydrochloride, and 2.5 mL (0.018 mole) of TEA in 50 mL of ethanol was stirred at ambient temperature for about four hours. The reaction mixture was then concentrated under reduced pressure to near-dryness. The residue was taken up in 100 mL of water and extracted with three 75 mL portions of methylene chloride. The combined extracts were washed with 75 mL of aqueous 10% lithium chloride solution and dried with sodium sulfate. The mixture was filtered and concentrated under reduced pressure to a residue. The residue was purified using column chromatography on silica gel, eluting with ethyl acetate-chloroform mixtures. The product-containing fractions were combined and concentrated under reduced pressure, yielding 0.6 gram of Compound 15, mp 46–49° C. The NMR spectrum was consistent with the proposed structure. The reaction was repeated several times on a larger scale.

EXAMPLE 2

Synthesis of N-[4-(ethoxyiminomethyl)phenylmethyl]4-[bis(4-trifluoromethoxyphenyl)hydroxymethyl]piperidine N-oxide (Compound 16)

A solution of 22.7 grams (0.030 mole) of N-[4-(ethoxyiminomethyl)phenylmethyl]-4-[bis(4-trifluoromethoxyphenyl)hydroxymethyl]piperidine and 50 mL of 30% hydrogen peroxide in 300 mL of methanol was stirred at ambient temperature for about 16 hours. After this time the reaction mixture was diluted with 500 mL of water and extracted with three 200 mL portions of ethyl acetate. The combined extracts were washed with 200 mL of aqueous 10% lithium chloride. The organic layer was dried with sodium sulfate and filtered. The filtrate was concentrated under reduced pressure to a residue. The residue was purified using column chromatography on silica gel, eluting with methanol-methylene chloride mixtures. The product-containing fractions were combined and concentrated under reduced pressure, yielding 22.1 grams of Compound 16, mp 188–191° C. The NMR spectrum was consistent with the proposed structure.

Table 1 below shows representative compounds of the present invention.

TABLE 1

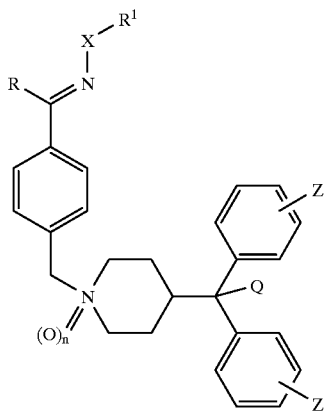

where Q is hydroxy

| Cmpd No | R | $R^1$ | n | X | Z |
|---|---|---|---|---|---|
| 1 | H | H | 0 | O | 4-$CF_3$ |
| 2 | H | H | 1 | O | 4-$CF_3$ |
| 3 | H | $CH_3$ | 0 | O | 4-$CF_3$ |
| 4 | H | $CH_3$ | 1 monohydrate | O | 4-$CF_3$ |
| 5 | H | $C_2H_5$ | 0 | O | 4-$CF_3$ |

TABLE 1-continued

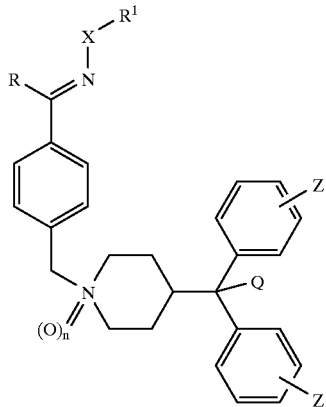

| | | | | | |
|---|---|---|---|---|---|
| 6 | H | $C_2H_5$ | 1 | O | 4-$CF_3$ |
| 7 | H | n-$C_3H_7$ | 0 | O | 4-$CF_3$ |
| 8 | H | i-$C_3H_7$ | 1 | O | 4-$CF_3$ |
| 9 | H | $C_2H_4OCH_3$ | 0 | O | 4-$CF_3$ |
| 10 | $OCH_3$ | $C_2H_5$ | 0 | O | 4-$CF_3$ |
| 11 | $N(CH_3)_2$ | $CH_3$ | 0 | O | 4-$CF_3$ |
| 12 | $N(CH_3)_2$ | $CH_3$ | 1 | O | 4-$CF_3$ |
| 13 | H | H | 0 | O | 4-$OCF_3$ |
| 14 | H | $CH_3$ | 0 | O | 4-$OCF_3$ |
| 15 | H | $C_2H_5$ | 0 | O | 4-$OCF_3$ |
| 16 | H | $C_2H_5$ | 1 | O | 4-$OCF_3$ |
| 17 | H | i-$C_3H_7$ | 0 | O | 4-$OCF_3$ |
| 18 | H | n-$C_3H_7$ | 1 | O | 4-$OCF_3$ |
| 19 | H | $C_3H_6OCH_3$ | 1 | O | 4-$OCF_3$ |
| 20 | $CH_3$ | H | 0 | O | 4-$OCF_3$ |
| 21 | $CH_3$ | $CH_3$ | 0 | O | 4-$OCF_3$ |
| 22 | $CH_3$ | $C_2H_5$ | 0 | O | 4-$OCF_3$ |
| 23 | $OC_2H_5$ | $C_2H_5$ | 0 | O | 4-$OCF_3$ |
| 24 | H | $C_2H_5$ | 0 | O | 4-$SF_5$ |
| 25 | H | $C_2H_5$ | 1 | O | 4-$SF_5$ | where Q is hydroxy, X is $NR^2$

| Cmpd No | R | $R^1$ | $R^2$ | n | Z |
|---|---|---|---|---|---|
| 26 | $CH_3$ | —$C_2H_4OC_2H_4$— | | 0 | 4-$CF_3$ |
| 27 | H | $CH_2CF_3$ | H | 0 | 4-$OCF_3$ |
| 28 | H | $CH_3$ | $CH_3$ | 0 | 4-$OCF_3$ |
| 29 | $CH_3$ | $CH_3$ | $CH_3$ | 0 | 4-$OCF_3$ |
| 30 | H | —$C_4H_8$— | | 0 | 4-$OCF_3$ |
| 31 | $CH_3$ | —$C_4H_8$— | | 0 | 4-$OCF_3$ |
| 32 | H | —$C_2H_4OC_2H_4$— | | 0 | 4-$OCF_3$ |
| 33 | H | $CH_3$ | $CH_3$ | 0 | 4-$SF_5$ |
| 34 | $CH_3$ | —$C_2H_4OC_2H_4$— | | 0 | 4-$OCF_3$ |
| 35 | H | $C_4H_9$ | $CO_2CH_3$ | 0 | 4-$CF_3$ |
| 36 | H | $C_4H_9$ | $COCH_3$ | 0 | 4-$CF_3$ |
| 37 | H | $C_4H_9$ | $CO_2CH_3$ | 0 | 4-$OCF_3$ |
| 38 | H | $C_4H_9$ | $COCH_3$ | 0 | 4-$OCF_3$ | where Q is Hydroxy

| Cmpd No | R | $R^1$ | n | X | Z |
|---|---|---|---|---|---|
| 39 | H | $CH_3$ | 1 ethanesulfonic acid salt | O | 4-$CF_3$ |
| 40 | H | $C_2H_5$ | 0 HCl salt | O | 4-$CF_3$ |
| 41 | H | i-$C_3H_7$ | 0 | O | 4-$CF_3$ |
| 42 | H | n-$C_3H_7$ | 1 | O | 4-$CF_3$ |
| 43 | H | $CH_2CH_2F$ | 0 | O | 4-$CF_3$ |
| 44 | H | $CONHC_2H_5$ | 0 | O | 4-$CF_3$ |
| 45 | H | $COCH(CH_3)_2$ | 0 | O | 4-$CF_3$ |
| 46 | H | $CH_2CH_2F$ | 1 | 0 | 4-$CF_3$ |
| 47 | H | $COCH(CH_3)_2$ | 1 | O | 4-$CF_3$ |
| 48 | H | $COCH_3$ | 0 | O | 4-$CF_3$ |
| 49 | H | $CONHCH_3$ | 0 | O | 4-$CF_3$ |
| 50 | Cl | $C_2H_5$ | 0 | O | 4-$CF_3$ |

TABLE 1-continued

| | | R¹ |
| | X/ | |
| R—C | | |
| | N | |

(structure: substituted benzyl piperidine with diphenylmethyl-Q group, N-oxide (O)ₙ, phenyl rings bearing Z substituents)

| Cmpd No | R | R¹ | n | X | Z |
|---|---|---|---|---|---|
| 51 | H | $C_2H_5$ | 1 ethanesulfonic acid salt | O | 4-$CF_3$ |
| 52 | H | $CONHCH_3$ | 1 | O | 4-$CF_3$ |
| 53 | H | $COCH(CH_3)_2$ | 0 | O | 4-$OCF_3$ |
| 54 | H | $COCH_3$ | 0 | O | 4-$OCF_3$ |
| 55 | H | $CH_2CH_2F$ | 0 | O | 4-$OCF_3$ |
| 56 | H | $CONHC_2H_5$ | 0 | O | 4-$OCF_3$ |
| 57 | H | $CH_3$ | 1 | O | 4-$OCF_3$ |
| 58 | H | $CH_3$ | 0 | O | 4-$SF_5$ |
| 59 | H | $CH_3$ | 1 | O | 4-$SF_5$ |
| 60 | H | $CH_3$ | 0 | O | 3-$OCF_2$O-4 |
| 61 | H | $CH_3$ | 1 | O | 3-$OCF_2$O-4 |
| 62 | H | $CH_3$ | 0 | O | 4-$SCF_3$ |
| 63 | H | $CH_3$ | 1 | O | 4-$SCF_3$ |
| 64 | H | $C_2H_5$ | 0 | O | 3-$OCF_2$O-4 |
| 65 | H | $C_2H_5$ | 1 | O | 3-$OCF_2$O-4 |
| 66 | H | $C_2H_5$ | 0 | O | 4-$SCF_3$ |
| 67 | H | $C_2H_5$ | 1 | O | 4-$SCF_3$ |
| 68 | H | $CH_3$ | 0 | O | 4-$SOCF_3$ |
| 69 | H | $CH_3$ | 1 | O | 4-$SOCF_3$ |
| 70 | H | $CH_3$ | 0 | O | 4-$SO_2CF_3$ |
| 71 | H | $CH_3$ | 1 | O | 4-$SO_2CF_3$ |
| 72 | H | $C_2H_5$ | 0 | O | 4-$SOCF_3$ |
| 73 | H | $C_2H_5$ | 1 | O | 4-$SOCF_3$ |
| 74 | H | $C_2H_5$ | 0 | O | 4-$SO_2CF_3$ |
| 75 | H | $C_2H_5$ | 1 | O | 4-$SO_2CF_3$ | where Q is fluoro

| Cmpd No | R | R¹ | n | X | Z |
|---|---|---|---|---|---|
| 76 | H | $CH_3$ | 0 | O | 4-$CF_3$ |
| 77 | H | $CH_3$ | 1 | O | 4-$CF_3$ |
| 78 | H | $CH_3$ | 0 | O | 4-$OCF_3$ |
| 79 | H | $CH_3$ | 1 | O | 4-$OCF_3$ |
| 80 | H | $C_2H_5$ | 0 | O | 4-$CF_3$ |
| 81 | H | $C_2H_5$ | 1 | O | 4-$CF_3$ |
| 82 | H | $C_2H_5$ | 0 | O | 4-$OCF_3$ |
| 83 | H | $C_2H_5$ | 1 | O | 4-$OCF_3$ |

TABLE 2

Characterizing Data

| Cmpd. No. | MP (C.°)/ Physical State | Cmpd. No. | MP (C.°)/ Physical State | Cmpd. No. | MP (C.°)/ Physical State |
|---|---|---|---|---|---|
| 1 | 108–117 | 2 | 217–221 dec | 3 | 65–71 |
| 4 | 195–203 | 5 | 60–65 | 6 | 207–210dec |
| 7 | 50–59 | 8 | 201–205 | 11 | 66–68 |
| 12 | 165–168 | 13 | 91–97 | 14 | 47–52 |
| 15 | 46–49 | 16 | 188–191 | 20 | 87–94 |
| 21 | 56–62 | 22 | 56–62 | 27 | 56–62 |
| 28 | 58–65 | 29 | 51–55 | 30 | 69–72 |
| 31 | 49–58 | 32 | 75–81 | 34 | 63–67 |
| 41 | 85–88 | 42 | 200–205 | 43 | 63–68 |
| 44 | 178–179 | 45 | 78–87 | 46 | 203–205 |
| 47 | 130–140 | 48 | 78–87 | 49 | 98–105 |
| 50 | Oil | 51 | 202–209 | 52 | 184–194 |
| 53 | 65–70 | 54 | 73–82 | 55 | Oil |
| 56 | 138–145 | | | | |

Biological Testing

Candidate insecticides were evaluated for activity against tobacco budworm (*Heliothis virescens* [Fabricius]) by applications to the surface of a wheat germ-based artificial insect diet. Solutions of the candidate insecticides were prepared for testing by diluting a standard 50 millimolar DMSO solution of each candidate insecticide with DMSO, then further diluting with a 1:1 water/acetone solution (V/V). Forty microliters of this solution of calculated concentration was then pipetted onto the surface of the diet in each of six containers, to provide six replicates for each rate of application. Once treated, the contents of the containers were allowed to dry, leaving the calculated concentration (in millimoles) of candidate insecticide on the surface of the diet. In each container was placed one second instar tobacco budworm larvae. The container was sealed with a transparent film, and then held in a growth chamber for five days. After the five-day exposure period the insecticidal activity of the candidate insecticide was recorded as percent mortality when compared to the total number of insects infested.

The compounds of the present invention were tested in the laboratory as solutions in DMSO. It is expected that all formulations normally employed in applications of insecticides would be usable with the compounds of the present invention. These include wettable powders, emulsifiable concentrates, water suspensions, flowable concentrates, and the like.

Insecticidal activity at a selected molar concentration of test chemical are given for various compounds of this invention in Table 3. The test compounds are identified by numbers which correspond to those in Table 1.

TABLE 3

Insecticidal Activity of Test Compounds Applied to the Surface of the Diet of Tobacco Budworm Compound No.

| 1 | 2 | 3 | 4 | 5 | 6 | 7 | 8 | 11 |
|---|---|---|---|---|---|---|---|---|
| | | | Percent Mortality | | | | | |
| 100 | 67 | 100 | 100 | 100 | 100 | 100 | 100 | 67 |

Compound No.

| 12 | 13 | 14 | 15 | 16 | 20 | 21 | 22 | 27 |
|---|---|---|---|---|---|---|---|---|
| | | | Percent Mortality | | | | | |
| 100 | 100 | 100 | 100 | 100 | 100 | 100 | 100 | 100 |

Compound No.

| 28 | 29 | 30 | 31 | 32 | 34 | 41 | 42 | 43 |
|---|---|---|---|---|---|---|---|---|

TABLE 3-continued

Insecticidal Activity of Test Compounds Applied to the Surface
of the Diet of Tobacco Budworm
Percent Mortality

| 100 | 17 | 100 | 0 | 50 | 67 | 100 | 50* | 100 |
|---|---|---|---|---|---|---|---|---|

Compound No.

| 44 | 45 | 46 | 47 | 48 | 49 | 50 | 51 | 52 |
|---|---|---|---|---|---|---|---|---|

Percent Mortality

| 83 | 100 | 100 | 100 | 67 | 50 | 50 | 100 | 83 |
|---|---|---|---|---|---|---|---|---|

Compound No.

| 53 | 54 | 55 | 56 |
|---|---|---|---|

Percent Mortality

| 100 | 100 | 100 | 83 |
|---|---|---|---|

Unless otherwise noted the concentration of candidate insecticide on the surface of the diet is 0.025 millimoles
*Concentration of candidate insecticide on the surface of the diet is 0.0025 millimoles For insecticidal application, the active compounds are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of the present compounds. Such granular formulations are free-flowing, non-dusty, and readily water-soluble or water-miscible. The soluble or dispersible granular formulations described in U.S. Pat. No. 3,920,442 are useful herein with the present insecticidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active insecticidal compounds of this invention may be formulated and/or applied with other insecticides, fungicides, nematicides, plant growth regulators, fertilizers, or other agricultural chemicals. In using an active compound of this invention, whether formulated alone or with other agricultural chemicals, to control insects, an effective amount and concentration of the active compound is applied to the locus where control is desired. The locus may be, e.g., the insects themselves, plants upon which the insects feed, or the insect habitat. When the locus is the soil, e.g., soil in which agricultural crops have been or will be planted, the composition of the active compound may be applied to and optionally incorporated into the soil. For most applications the effective amount may be as low as, e.g. about 10 to 500 g/ha, preferably about 100 to 250 g/ha.

It is apparent that various modifications may be made in the formulation and application of the compounds of this invention without departing from the inventive concepts herein as defined in the claims.

We claim:

1. A compound having the formula

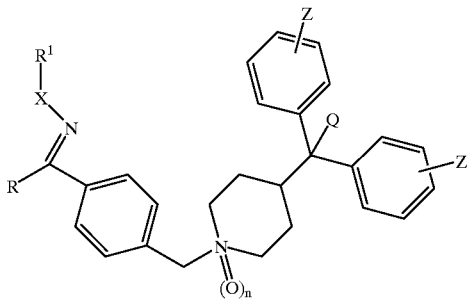

I where

R is hydrogen, halogen, alkyl, alkoxy, dialkylamino;

$R^1$ is hydrogen, alkyl, haloalkyl, alkoxyalkyl, alkylcarbonyl and alkylaminocarbonyl;

Q is fluoro or hydroxy;

X is oxygen or $NR^2$

Z is halogen, haloalkyl, haloalkoxy, pentahalothio, haloalkylthio, haloalkylsulfinyl, haloalkylsulfonyl, and —$OCF_2O$— attached to two adjacent carbon atoms of the phenyl ring;

n is 0 or 1;

when X is $NR^2$, $R^2$ is hydrogen, alkyl, alkylcarbonyl, alkoxycarbonyl, or $R^1$ and $R^2$ taken together may be —$C_mH_{2m}$—, or —$C_2H_4OC_2H_4$—, where m is 3–9; and their agriculturally acceptable salts.

2. The compound of claim 1 where R is hydrogen; $R^1$ is alkyl; Q is hydroxy; X is oxygen; Z is trifluoromethyl or trifluoromethoxy; n is 0 or 1; and their agriculturally acceptable salts.

3. The compound of claim 2 which is N-[4-(ethoxyiminomethyl)phenylmethyl]-4-[bis(4-trifluoromethoxyphenyl)hydroxymethyl]piperidine N-oxide; and its agriculturally acceptable salts.

4. An insecticidal composition comprising an insecticidally effective amount of a compound of claim 1, and an insecticidally compatible carrier.

5. An insecticidal composition comprising an insecticidally effective amount of a compound of claim 2, and an insecticidally compatible carrier.

6. An insecticidal composition comprising an insecticidally effective amount of the compound of claim 3, and an insecticidally compatible carrier.

7. A method of controlling insects, comprising applying an insecticidally effective amount of a composition of claim 4 to a locus where insect control is desired.

8. A method of controlling insects, comprising applying an insecticidally effective amount of a composition of claim 5 to a locus where insect control is desired.

9. A method of controlling insects, comprising applying an insecticidally effective amount of a composition of claim 6 to a locus where insect control is desired.

10. The compound of claim 2 which is N-[4-(ethoxyiminomethyl)phenylmethyl]-4-[bis(4-trifluoromethoxyphenyl)hydroxymethyl]piperidine; and its agriculturally acceptable salts.

11. The compound of claim 2 which is N-[4-(ethoxyiminomethyl)phenylmethyl]-4-[bis(4-trifluoromethylphenyl)hydroxymethyl]piperidine N-oxide; and its agriculturally acceptable salts.

12. The compound of claim 2 which is N-[4-(ethoxyiminomethyl)phenylmethyl]-4-[bis(4-trifluoromethylphenyl)hydroxymethyl]piperidine; and its agriculturally acceptable salts.

13. The compound of claim 1, which is selected from the group consisting of Compounds 1–83 of Table 1.

14. An insecticidal composition comprising an insecticidally effective amount of the compound of claim 10, and an insecticidally compatible carrier.

15. An insecticidal composition comprising an insecticidally effective amount of the compound of claim 11, and an insecticidally compatible carrier.

16. An insecticidal composition comprising an insecticidally effective amount of the compound of claim 12, and an insecticidally compatible carrier.

17. An insecticidal composition comprising an insecticidally effective amount of the compound of claim 13, and an insecticidally compatible carrier.

18. A method of controlling insects, comprising applying an insecticidally effective amount of a composition of claim 14 to a locus where insect control is desired.

19. A method of controlling insects, comprising applying an insecticidally effective amount of a composition of claim 15 to a locus where insect control is desired.

20. A method of controlling insects, comprising applying an insecticidally effective amount of a composition of claim 16 to a locus where insect control is desired.

* * * * *